United States Patent
Cen et al.

(10) Patent No.: US 11,253,319 B2
(45) Date of Patent: Feb. 22, 2022

(54) OSTEOTOMY GUIDE PLATE AND PREPARATION METHOD THEREOF

(71) Applicant: CENTERMED, INC, Walnut Creek, CA (US)

(72) Inventors: Xin Cen, Walnut Creek, CA (US); Chen Yang, Walnut Creek, CA (US)

(73) Assignee: CenterMed, Inc., Walnut Creek, CA (US)

( * ) Notice: Subject to any disclaimer, the term of this patent is extended or adjusted under 35 U.S.C. 154(b) by 241 days.

(21) Appl. No.: 16/409,849

(22) Filed: May 12, 2019

(65) Prior Publication Data
US 2020/0281655 A1  Sep. 10, 2020

(30) Foreign Application Priority Data
Mar. 4, 2019 (CN) .......................... 201910160400.1

(51) Int. Cl.
*A61B 34/10* (2016.01)
*A61B 17/17* (2006.01)
(Continued)

(52) U.S. Cl.
CPC ............ *A61B 34/10* (2016.02); *A61B 17/151* (2013.01); *A61B 17/176* (2013.01);
(Continued)

(58) Field of Classification Search
CPC ............................... A61B 34/10; A61B 17/151
See application file for complete search history.

(56) References Cited

U.S. PATENT DOCUMENTS 9,317,634 B2 *  4/2016  Davison .................. G06F 30/20
9,707,044 B2    7/2017  Davison et al.
(Continued)

FOREIGN PATENT DOCUMENTS

CN      204446013 U    7/2015
CN      105916455 A    8/2016
(Continued)

OTHER PUBLICATIONS

First Office Action of priority application CN201910160400.1 dated Aug. 13, 2019.
(Continued)

*Primary Examiner* — Christian A Sevilla
(74) *Attorney, Agent, or Firm* — Muncy, Geissler, Olds & Lowe, P.C.

(57) ABSTRACT

The invention discloses an osteotomy guide plate and a preparation method thereof. The osteotomy guide plate comprises a substrate, an osteotomy guide standardized part, a guide plate retention hole, a nail hole and a drainage channel; wherein the guide plate retention hole is distributed on the surface of the substrate; the outer end side of the nail hole is integrally formed with a standardized sleeve, and a detachably connected protective inner sleeve standardized part is provided within the standardized sleeve. The preparation method comprises parameter design and model printing, wherein an innovative nail hole positioning method is used in the parameter design. The invention is suitable for the osteotomy operation of different parts, with the advantages of convenient production, high precision and long service life; the preparation method improves the accuracy of opening a hole on the osteotomy guide plate.

4 Claims, 4 Drawing Sheets

(51) Int. Cl.
  *B33Y 50/02* (2015.01)
  *B33Y 80/00* (2015.01)
  *B29C 64/393* (2017.01)
  *A61B 17/15* (2006.01)
  *B29L 31/00* (2006.01)
  *A61B 17/00* (2006.01)
  *B33Y 10/00* (2015.01)

(52) U.S. Cl.
  CPC ........ *A61B 17/1764* (2013.01); *B29C 64/393* (2017.08); *B33Y 50/02* (2014.12); *B33Y 80/00* (2014.12); *A61B 2017/00526* (2013.01); *A61B 2034/105* (2016.02); *A61B 2034/108* (2016.02); *B29L 2031/753* (2013.01); *B33Y 10/00* (2014.12)

(56) References Cited

U.S. PATENT DOCUMENTS

| | | | |
|---|---|---|---|
| 2011/0172672 A1* | 7/2011 | Dubeau | A61B 17/152 606/87 |
| 2011/0213376 A1* | 9/2011 | Maxson | A61B 17/151 606/88 |
| 2012/0226094 A1 | 9/2012 | Ritchey et al. | |
| 2013/0041381 A1* | 2/2013 | Clair | A61B 90/10 606/96 |
| 2014/0309644 A1* | 10/2014 | Metzger | A61B 17/1659 606/87 |
| 2014/0350614 A1* | 11/2014 | Frey | A61B 5/05 606/86 R |
| 2016/0143677 A1* | 5/2016 | Furrer | A61B 17/8071 606/280 |
| 2016/0342766 A1 | 11/2016 | Darwood | |
| 2017/0273718 A1* | 9/2017 | Metzger | A61B 17/58 |

FOREIGN PATENT DOCUMENTS

| | | |
|---|---|---|
| CN | 106361452 A | 2/2017 |
| CN | 206120431 U | 4/2017 |
| CN | 106618672 A | 5/2017 |
| CN | 107343817 A | 11/2017 |
| CN | 107928818 A | 4/2018 |
| CN | 107951538 A | 4/2018 |
| CN | 207785234 U | 8/2018 |
| CN | 108478251 A | 9/2018 |
| CN | 108606823 A | 10/2018 |
| CN | 208492220 U | 2/2019 |
| RO | 130310 A2 | 6/2015 |

OTHER PUBLICATIONS

Second Office Action of priority application CN201910160400.1 dated Dec. 13, 2019.
Third Office Action of priority application CN201910160400.1 dated Mar. 6, 2020.
Fourth Office Action of priority application CN201910160400.1 dated Jun. 24, 2020.
Notification of Patent Grant for Invention of priority application CN201910160400.1 dated Jul. 16, 2020.

* cited by examiner

OSTEOTOMY GUIDE PLATE AND PREPARATION METHOD THEREOF

CROSS-REFERENCE TO RELATED APPLICATIONS

This non-provisional application claims priority to and benefit of, under 35 U.S.C. § 119(a), Patent Application No. 201910160400.1, filed in P.R. China on Mar. 4, 2019, the entire content of which is hereby incorporated by reference.

FIELD OF THE INVENTION

The present disclosure relates to the field of digitized medical surgery, in particular, to an osteotomy guide plate and a preparation method.

BACKGROUND OF THE INVENTION

Digital medical treatment is a new type of modern medical treatment that applies modern computer technology and information technology to the whole process of medical treatment, and also indicates the trend and management goal of public medical care. The emergence of digital medical equipment has greatly enriched the content and capacity of medical information. As one of the world's top technologies, 3D printing is deeply integrated with the medical industry and has become an indispensable technology for surgery, which promotes the realization of precision medical treatment. The application of 3D printing technology in the field of oral and maxillofacial surgery is of great significance, and in particular, the use of 3D printed osteotomy guide plate in plastic surgery, orthognathic surgery, and tumor-removing surgery and the like effectively improves the accuracy of surgery and shortens the operation time. As a powerful tool for achieving precision surgery, an osteotomy guide plate is formed through digitized design and 3D printing based on 3D reconstruction and surgical simulation. In the surgery for reconstructing a defective mandible by using an autologous bone, it can plan out the osteotomy line and osteotomy coverage for the doctor, and cut the autologous bone such as the fibula, rib and the like into a suitable length for reconstruction, thereby shortening the operation time and improving the safety of the surgery.

A Chinese utility model patent discloses a fibula osteotomy guide plate and a positioning device for fibula osteotomy, the fibula osteotomy guide plate comprising a guide plate body and a positioning portion; the positioning portion comprising a first positioning portion and a second positioning portion, the first positioning portion disposed at one end of the body of the guide plate, and the second positioning portion disposed at the other end of the body of the guide plate; and the first positioning portion and the second positioning portion both provided with a cutting groove, the cutting groove being a through groove. The positioning device for fibula osteotomy comprises at least two of the fibula osteotomy guide plate, wherein a second positioning portion of one of the fibula osteotomy guide plates is fixedly coupled to the first positioning portion of the other fibula osteotomy guide plate and forms an X-shape. The patented fibula osteotomy guide plate can improve the accuracy of the fibula osteotomy surgery by the medical personnel through simple operation and lower requirements for the experience of the surgeon, which avoids the surgical operation error caused by the surgeon's sensational operation. The positioning device for fibula osteotomy provided by such patent can provide multiple cut-offs to ensure the fibula osteotomy and shaping according to the predetermined design, and improve the success rate of the surgery.

However, as the existing osteotomy guide plates perform the positioning and fixing of a nail hole by the same hole site, the above process not only needs to completely rely on the guide plate retention hole on the osteotomy guide plate to perform the guiding, but also needs to be implemented many times. As such, the osteotomy guide plate, especially at the place near the guide plate retention hole, is easy to be damaged, resulting in many problems such as inaccurate nail hole guidance and easy deviation of direction. In addition, the existing osteotomy guide plates are either not provided with a drainage hole, in which case, the debris generated by the surgeon in drilling during the surgery may damage the body of the fixed guide plate and increase the risk of surgery; or provided with a drainage hole under the guide plate retention hole, but in which case, the aperture of the drainage hole is limited by the existence of the nail hole, which causes problems such as the debris generated during the intraoperative drilling easy to block the drainage hole, and bad drainage effect.

In addition, regarding the way to open the nail hole, in the prior art, such hole is often formed by placing a physical marker such as a gauge pin or a tack into the existing nail hole. After the physical marker is placed securely, a three-dimensional scan is performed, and then the model file of the scan result is imported into the design program to perform the positioning of perforating to the guide plate to be provided with the nail hole. For example, a Chinese invention patent discloses a mandibular restoration device and a preparation method thereof, the preparation method comprising fixing a mandibular reconstruction plate to a post-operative mandibular model, drilling in the post-operative mandibular model in a place corresponding to the mounting hole site of the mandibular metal bone plate, wherein in the process of drilling in the post-operative mandibular model, a set of gauge pins are used to locate the center of the hole site, and the center of the hole site is located by: according to the diameter of the mounting hole of the shaped mandibular metal bone plate, selecting a gauge pin with a matching diameter and inserting it into the mounting hole vertically, locating the center of the mounting hole to drill in the post-operative mandibular model. Such a method for perforating a nail hole not only tends to change the relative position of the physical marker at the time of opening, leading to positioning error, but also tends to generate an artifact on the model during the three-dimensional scanning process, which affects the accuracy of the opening.

SUMMARY OF THE INVENTION

One of the objectives of the present invention is to overcome the defects described in the prior art, thereby providing an osteotomy guide plate. The osteotomy guide plate provided by the present invention mainly comprises standardized parts, each of which is of a plurality of types, such that the combined osteotomy guide plate may be adjusted according to the specifications of the standardized parts to adapt to the osteotomy operation in different parts. The osteotomy guide plate is easy to produce, highly accurate, and of long service life, which greatly improves the surgeon's surgical success rate.

In order to achieve the above objective, the present invention provides the following technical solutions:

an osteotomy guide plate, comprising: a substrate; and a guide plate retention hole and a nail hole respectively disposed on the substrate;

the guide plate retention hole is distributed on the surface of the substrate fixing the substrate on the bone in the operation area;

the end portion of the nail hole is formed with a standardized sleeve, and a detachably connected protective inner sleeve standardized part is provided within the standardized sleeve, and the protective inner sleeve standardized part is used for guiding and positioning the direction of perforating for a drilling device; preferably, the outer end portion of the nail hole is formed with the standardized sleeve.

Compared with the existing osteotomy guide plate, the osteotomy guide plate provided by the present invention is suitable for all types of bones in the operation area. Other components except the substrate are standardized parts. The standard parts involved in the invention can be mass-produced, avoiding the first one-to-one production of the individual substrates, and then the individualized osteotomy guides and the like according to the substrate design in the prior art, thereby greatly improving the efficiency in producing the osteotomy guide plate. Moreover, since most of the components in the present invention are standardized parts, the standardized parts are free of significant layering when performing the 3D printing. In particular, the substrates of the cuboid standardized parts are kept from high risk of damage caused by uneven stress transfer when subjecting to external force.

In addition, the present invention is designed to divide the conventional hole site into two parts, one of which is a guide plate retention hole matched with a screw for fixing the substrate to the bone in the operation area, and the other is for guiding and positioning the direction of perforating for the drilling device, wherein the nail hole corresponds to the mounting hole on the metal graft, and the guide plate retention hole is matched with the retaining screw, such that each hole site performs its own function, which greatly reduces damage to the substrate around the nail hole and improves the yield of the osteotomy guide plate during the preparation. In addition, the nail hole of the present invention is different from the prior art in that a standardized sleeve is integrally formed on the outer end side of the nail hole. The standardized sleeve is a standardized part suitable for each nail hole on the substrate. This standardized structure can avoid the breakage of the substrate caused by the conventional nail holes. In addition, a detachably connected protective inner sleeve standardized part is provided within the standardized sleeve. The standardized sleeve and the protective inner sleeve standardized part form an assembly. The two are locked to each other, which can greatly enhance the strength of the assembly. When designing such a structure, the engineer only needs to match the standardized part imported when designing the nail hole of each substrate. It substantially improves the design efficiency of the engineer. In addition, by providing the standardized sleeve and the protective inner sleeve standardized part, it avoids excessive damage to the substrate even if the drilling tool needs to be guided through the drill hole multiple times. It further improves the yield of the osteotomy guide plate.

The shape of the inner wall of the substrate is adapted to the shape of the bone in the operation area; the osteotomy guide plate could be a jawbone osteotomy guide plate or a fibula osteotomy guide plate, when the osteotomy guide plate is a jawbone osteotomy guide plate, the shape of the outer wall of the substrate is adapted to the shape of the bone in the operation area; and when the osteotomy guide plate is a fibula osteotomy guide plate, the substrate is a cuboid standardized part.

The osteotomy guide plate of the present invention further comprises an osteotomy guide standardized part disposed on the substrate; preferably, the osteotomy guide standardized part is provided with an osteotomy guide through groove, the osteotomy guide standardized part is provided in at least one; further preferably, the osteotomy guide through groove of each of the osteotomy guide standardized part corresponds to the osteotomy line in the operation area;

As an embodiment, the osteotomy guide standardized part is a plate-like structure, the osteotomy guide through groove is formed on the sidewall of the plate-like structure, and the depth of the osteotomy guide through groove in the width direction of the plate-like structure is greater than the thickness of the substrate.

Preferably, the outer end portion of the nail hole is integrally formed with a standardized sleeve, the inner wall of the standardized sleeve is provided with one groove, and the outer wall of the protective inner sleeve standardized part is provided with a prismoid adapted to the groove; preferably, the protective inner sleeve standardized part is locked by the prismoid in the groove of the standardized sleeve.

Preferably, the protective inner sleeve standardized part has a hardness greater than the standardized sleeve, and the standardized sleeve is made of photosensitive resin, and the protective inner sleeve standardized part is made of stainless steel or titanium alloy.

As another embodiment, the osteotomy guide plate is further provided with a drainage channel, where the drainage channel is distributed within the substrate, and the drainage channel is respectively communicated with the guide plate retention hole and/or the nail hole at one end, and with the outer ambient at the other end.

Preferably, the surface of the substrate is further provided with a convex mark.

Another one of the objectives of the present invention is providing a method for preparing an osteotomy guide plate is provided, said method provided by the invention can improve the accuracy in opening a hole site in the osteotomy guide plate and reduce the damage rate of the osteotomy guide plate.

In order to achieve the above objective, the present invention provides the following technical solutions:

A method for preparing an osteotomy guide plate, comprising the steps of:

A. Parameter Design creating data for the standardized part: using digital technology to create data for the osteotomy guide standardized part, the standardized sleeve, and the protective inner sleeve standardized part respectively for later use;

extracting data of the nail hole: importing a postoperative bone model and a postoperative bone graft model of a patient and conducting simulation matching, and obtaining a restoration model by 3D printing technology, shaping a metal graft with a mounting hole onto the restoration model, and perforating in the restoration model along the mounting hole to form a nail hole site; placing the restoration model with the nail hole site into a three-dimensional scanner for scanning to extract the data of the nail hole;

creating data of the hole-free guide plate: importing the model of the bone for osteotomy, and generating a model of the substrate; importing the data of the osteotomy guide standardized part, selecting the data of the osteotomy guide standardized part adapted to the substrate, and making the osteotomy guide through groove coincide with the osteotomy line; preferably, confirming the coverage area of the substrate and the position of the osteotomy line according to the surgical plan before said generating the model of the substrate; and creating data of the osteotomy guide plate: importing the data of the nail hole and the data of standardized sleeve, matching the data of standardized sleeve respectively with the data of the nail hole, and then creating a guide plate retention hole to complete the parameter design of the osteotomy guide plate;

B. Model Printing importing the parameters of the osteotomy guide into a 3D printer for printing, and then embedding the printed protective inner sleeve standardized part in the standardized sleeve to obtain the osteotomy guide plate.

Preferably, the extracting the data of the nail hole in the step A comprises establishing a fitting parameter cylinder on the space of the nail hole site, wherein the parameter distribution range of the fitting parameter cylinder covers the postoperative bone stump and the bone surface after the bone grafting.

Preferably, in the step A, the model of the bone for osteotomy is a preoperative mandibular model, the undulating condition of the inner side of the substrate is matched with that of the surface of the preoperative mandibular model, and the substrate covers the whole osteotomy line.

Preferably, in the step A, the model of the bone for osteotomy is a fibula model, and the substrate is a cuboid standardized part of a plurality of types, and the matching with the substrate comprises firstly generating a parameter fitting cuboid in the coverage area of the fibula model, and then selecting data of an appropriate cuboid standardized part to be imported, and matching the main inertia axis of the cuboid standardized part with the parameter cuboid to obtain a substrate matched to a suitable position.

Preferably, the matching in the step A is implemented by extracting a main inertia axis of the standardized sleeve through digital technique, such that the main inertia axis is matched with the data of the nail hole, while setting the distance between the top end of each of the standardized sleeve and the bone surface to a fixed value.

Preferably, the creating the guide plate retention hole in the step A comprises creating a cylinder with an expected size through digital technique, moving the cylinder for axially passing through the substrate model, and then cutting the substrate model by a Boolean operation function.

Preferably, the step A further comprises drawing a lumen curve of the drainage channel in the substrate by digital technique, and expanding the lumen curve into a lumen body.

Compared with the prior art, the present invention has the following benefits:

(1) Compared with the existing osteotomy guide plate, the osteotomy guide plate provided by the present invention is suitable for all types of bones in the operation area. Other components except the substrate are standardized parts. The standard parts involved in the invention can be mass-produced, avoiding the first one-to-one production of the individual substrates, and then the individualized osteotomy guides and the like according to the substrate design in the prior art, thereby greatly improving the efficiency in producing the osteotomy guide plate. Moreover, since most of the components in the present invention are standardized parts, the standardized parts are free of significant layering when performing the 3D printing. In particular, the substrates of the cuboid standardized parts are kept from high risk of damage caused by uneven stress transfer when subjecting to an external force.

In addition, the present invention is designed to divide the conventional hole site into a two parts, one of which is a guide plate retention hole matched with a screw for fixing the substrate to the bone in the operation area, and the other is for guiding and positioning the direction of perforating for the drilling device, wherein the nail hole corresponds to the mounting hole on the metal graft, and the guide plate retention hole is matched with the retaining screw, such that each hole site performs its own function, which greatly reduces damage to the substrate around the nail hole and improves the yield of the osteotomy guide plate during the preparation. In addition, the nail hole of the present invention is different from the prior art in that a standardized sleeve is integrally formed on the outer end side of the nail hole. The standardized sleeve is a standardized part suitable for each nail hole on the substrate. This standardized structure can avoid the breakage of the substrate caused by the conventional nail holes. In addition, a detachably connected protective inner sleeve standardized part is provided within the standardized sleeve. The standardized sleeve and the protective inner sleeve standardized part form an assembly. The two are locked to each other, which can greatly enhance the strength of the assembly. When designing such a structure, the engineer only needs to match the standardized part imported when designing the nail hole of each substrate. It substantially improves the design efficiency of the engineer. In addition, by providing the standardized sleeve and the protective inner sleeve standardized part, it avoids excessive damage to the substrate even if the drilling tool needs to be guided through the drill hole multiple times. It further improves the yield of the osteotomy guide plate. (2) The preparation method provided by the present invention mainly comprises two steps, i.e., the parameter design and then the model printing, wherein in the parameter design, the present invention uses an innovative nail hole positioning method, i.e., puncturing and perforating at a specified position, and then directly saving the model of the nail hole data with a 3D scanner for uses in the subsequent design processes. It is different from the existing nail hole method (first placing a positioning tool such as a tack or a gauge pin at a specified position, and then scanning with a 3D scanner the postoperative model, the metal graft, the positioning tool, etc., and then saving the resulted data for subsequent design flow) in that the nail hole design method of the invention does not need to place other additional components for three-dimensional scanning, which increases the scanning speed and does not have any artifact, thereby making the scanning result more accurate, and greatly reducing the risk of surgery caused by using such an osteotomy guide plate by the surgeon.

BRIEF DESCRIPTION OF THE DRAWINGS

In order to more clearly illustrate the embodiments of the present invention or the technical solutions in the prior art, the figures required for describing the embodiments or the prior art will be briefly described below. Obviously, the figures in the following description are only certain embodiments of the present invention, and other figures can be obtained based on these figures by those of ordinary skill in the art without any creative work.

DESCRIPTION OF THE REFERENCE NUMERALS

1. Substrate; 2. Osteotomy guide standardized part; 21. Osteotomy guide through groove; 3. Guide plate retention hole; 4. Nail hole; 41. Standardized sleeve; 5. Bone in the operation area; 6. Protective inner sleeve standardized part; 61. Prismoid; 7. Drainage channel; 8. Convex mark; 9. Metal bone plate; 91. Mounting hole.

DETAILED DESCRIPTION OF THE INVENTION

The technical solutions of the present invention will be clearly and completely described in the following with reference to the accompanying figures. It is obvious that the described embodiments are a part of the embodiments of the present invention, but not all of the embodiments. All other embodiments obtained by those of ordinary skill in the art based on the embodiments of the present invention without creative efforts are within the scope of the present invention.

In the description of the present invention, it is to be noted that the orientation or positional relationship indicated by terms "center", "upper", "lower", "left", "right", "vertical", "horizontal", "inner", "outer", etc. is based on the orientation or positional relationship shown in the figures, and is merely for a convenient and simplified description of the invention, rather than indicating or implying that the device or component of interest is in a specific orientation or constructed or operated in a specific orientation, and is therefore not to be construed as limiting the invention. In addition, the terms "first," "second," and "third" are used merely for description and are not to be construed as indicating or implying relative importance.

In the description of the present invention, it should be noted that the terms "installed", "connected", and "coupled" are to be understood broadly, such as fixed or detachably connected, or integrated coupled, unless otherwise explicitly defined and limited. It can be a mechanical connection or an electrical connection. It can be directly connected or indirectly connected through an intermediate medium, or the communication of the inner parts between two components. The specific meaning of the above terms in the present invention can be understood depending on specific cases by those skilled in the art.

In addition, the technical features involved in different embodiments of the present invention described below may be combined with each other as long as they do not constitute a conflict with each other.

Embodiment 1

Figure 1:
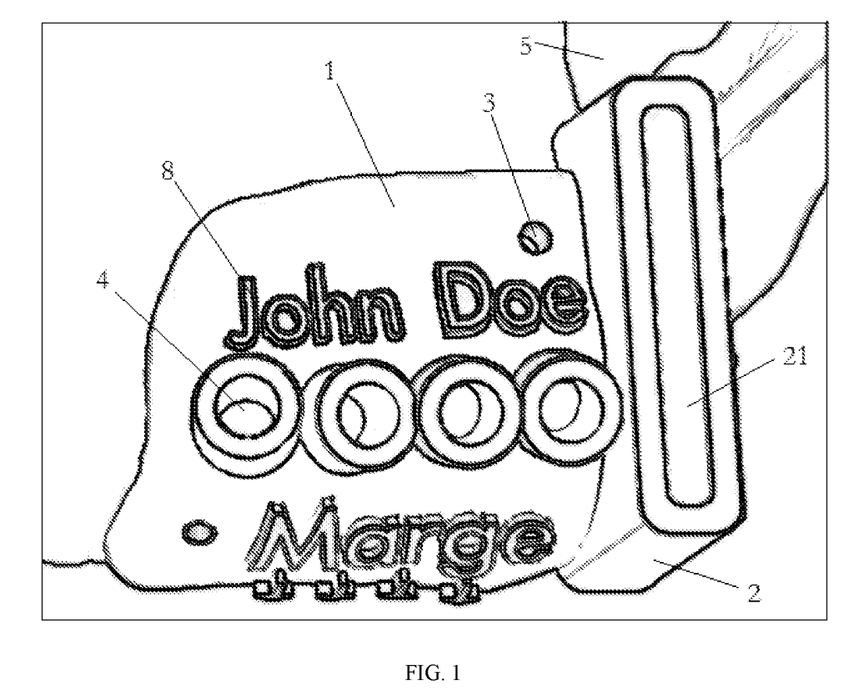
FIG. 1 is a schematic structural view of a mandibular osteotomy guide plate according to embodiment 1 of the present invention.

As shown in FIG. 1, the present invention provides a mandibular osteotomy guide plate, comprising a substrate 1 and an osteotomy guide standardized part 2, a guide plate retention hole 3 and a nail hole 4 respectively disposed on the substrate 1; wherein the substrate 1 is adapted to the shape of the bone (mandible) 5 in the operation area; the osteotomy guide standardized part 2 is provided with an osteotomy guide through groove 21, the osteotomy guide standardized part 2 is provided in at least one, and the osteotomy guide through groove 21 of each of the osteotomy guide standardized part 2 corresponds to the osteotomy line in the operation area; the guide plate retention hole 3 is distributed on the surface of the substrate 1 for matching with a screw to fix the substrate 1 on the bone 5 in the operation area; the outer end side of the nail hole 4 is integrally formed with a standardized sleeve 41, and a detachably connected protective inner sleeve standardized part 6 is provided within the standardized sleeve 41, and the protective inner sleeve standardized part 6 is used for guiding and positioning the direction of perforating for a drilling device.

In the osteotomy guide provided by the present invention, except for the substrate 1, the other components are standardized parts and are designed for different patients. It can be prepared simply by setting the substrate 1 according to the shape of the patient's mandible and assembling several other specified types of standardized parts compatible with the model on the substrate 1. The standardized parts involved in the invention can be mass-produced, which avoids firstly one-to-one production of personalized substrates, and then the design of personalized osteotomy guides and the like according to the substrate 1 in the prior art, thereby substantially improving the efficiency in producing the osteotomy guide plate. Moreover, since most of the components in the present invention are standardized parts, the standardized parts are free of significant layering when performing the 3D printing. In particular, the substrates of the cuboid standardized parts are kept from high risk of damage caused by uneven stress transfer when subjecting an to external force.

The osteotomy guide standardized part 2 in the present invention is a plate-like structure, and the osteotomy guide through groove 21 is provided on the sidewall of the plate-like structure. In addition, the depth of the osteotomy guide through groove 21 in the width direction of the structure is greater than the thickness of the substrate 1, whereby ensuring good guidance to the surgical scalpel from the osteotomy guide through groove 21. Of course, each substrate 1 may be provided with a plurality of osteotomy guide standardized part 2 as required by the actual osteotomy line. The osteotomy guide through groove 21 on each osteotomy guide standardized part 2 corresponds to the osteotomy line. The adjacent two osteotomy guide standardized parts 21 may also be arranged crosswise. At the intersection, the two osteotomy guide through grooves 21 involved are in communication, to facilitate the surgeon to cut from different angles.

Figure 6:
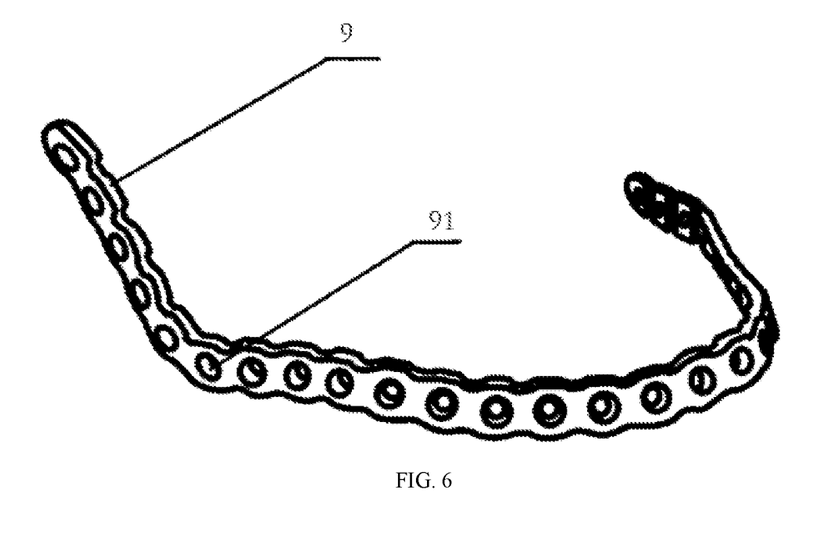
FIG. 6 is a schematic structural view of the structure of a metal bone plate used in the present invention.

As shown in FIG. 1, the guide plate retention hole 3 and the nail hole 4 are respectively disposed on the substrate of the present invention, instead of being used in combination as in the conventional osteotomy guide plate. In the present invention, the guide plate retention hole 3 is matched with a screw for fixing the substrate 1 to the bone 5 in the operation area. As shown in FIG. 6, the nail hole 4 corresponds to the mounting hole 91 on the metal bone plate 9 for guiding and positioning the direction of perforating for a drilling device. Therefore, each hole site performs its own duty, which greatly reduces the damage to the substrate 1 around the nail hole 4, and improves the yield of the osteotomy guide plate during the preparation.

Figure 3:
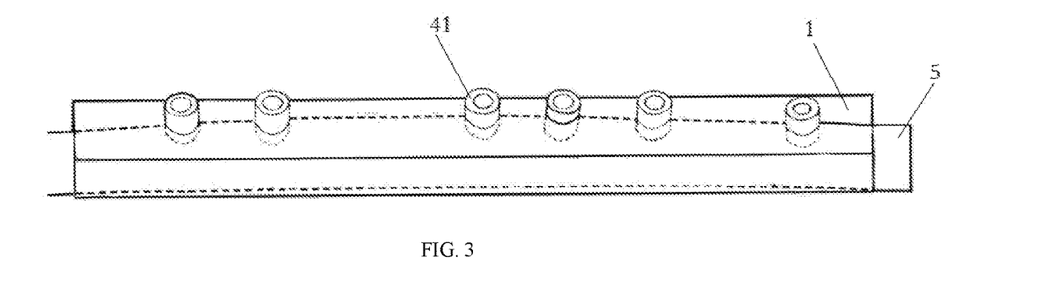
FIG. 3 is a schematic structural view of an embodiment of the present invention.
Figure 4:
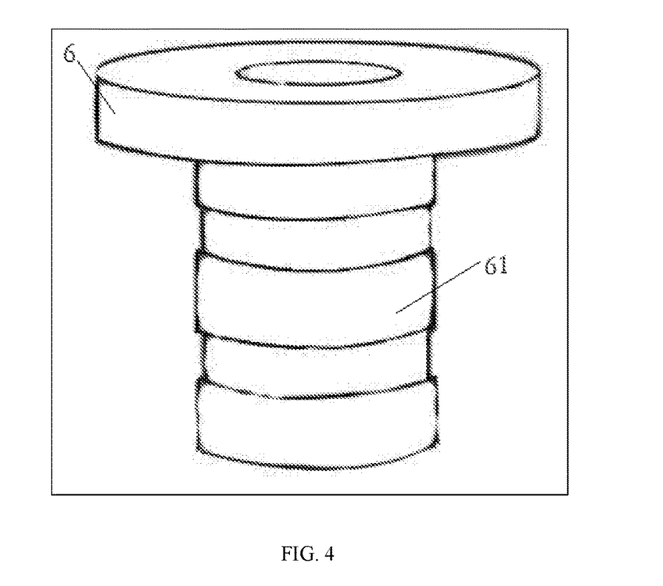
FIG. 4 is a schematic structural view of a protective inner sleeve standardized part according to an embodiment of the present invention.

In addition, as shown in FIG. 3, the present invention also integrally forms a standardized sleeve 41 on the outer end side of the nail hole 4. The standardized sleeve 41 is a standardized part suitable for each nail hole 4 on the substrate 1. This standardized structure can avoid breakage of the substrate 1 caused by the conventional nail hole 4. In addition, a detachably connected protective inner sleeve standardized part 6 is provided within the standardized sleeve 41. The standardized sleeve 41 and the protective inner sleeve standardized part 6 form an assembly. The two are locked to each other, which can greatly enhance the strength of the assembly. When designing such a structure, the engineer only needs to match the standardized part imported when designing the nail hole 4 of each substrate 1. It substantially improves the design efficiency of the engineer. In addition, by providing the standardized sleeve 41 and the protective inner sleeve standardized part 6, it avoids excessive damage to the substrate 1 even if the drilling tool needs to be guided through the drill hole multiple times. It further improves the yield of the osteotomy guide plate. In the present embodiment, at least one groove (not shown) is formed on the inner wall of the standardized sleeve 41. As shown in FIG. 4, the outer wall of the protective inner sleeve standardized part 6 is provided with a prismoid 61 adapted to the groove, and the protective inner sleeve standardized part 6 is locked in the groove of the standardized sleeve 41 by the prismoid 61. Of course, the inner wall of the standardized sleeve 41 can also be provided with a prismoid. In this condition, the outer wall of the inner sleeve standardized part 6 is provided with a matching groove to realize the locking after assembly. No matter how the inner sleeve standardized part 6 is locked, it has a hardness greater than that of the standardized sleeve 41. For example, the standardized sleeve 41 is made of photosensitive resin, and the inner sleeve standardized part 6 is made of stainless steel or titanium alloy.

Figure 2:
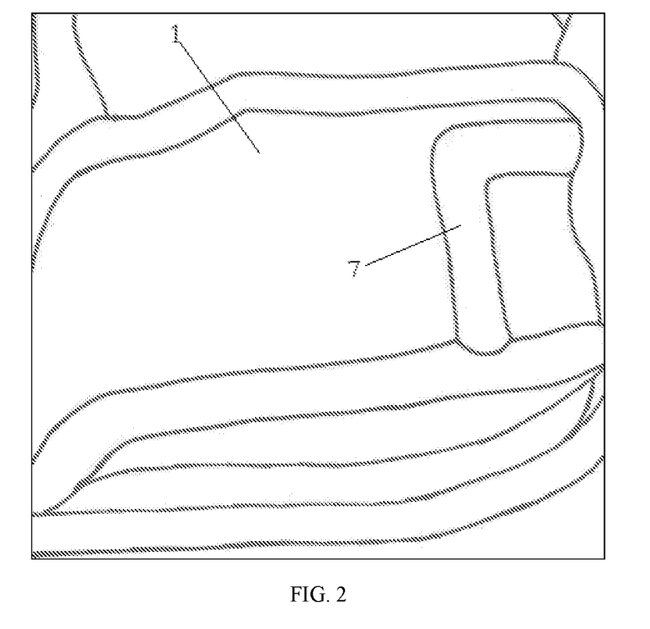
FIG. 2 is a perspective view of an embodiment of the present invention.

As an optional embodiment, as shown in FIG. 2, the present invention also provides a drainage channel 7 in the osteotomy guide plate, and compared to the practice of perforating a drainage hole near the nail hole 4 of the osteotomy guide plate, the drainage channel 7 of the present invention has the following features. The strip-shaped lumen of the drainage channel 7 is distributed between the guide plate retention hole 3 and the nail hole 4. The guide plate retention hole 3 and the nail hole 4 are communicated with the outer ambient. The channel has higher drainage efficiency with respect to the hole. Moreover, liquid such as physiological saline used for rinsing the bone fragments during the drilling process flows within the substrate through the drainage channel 7. It eventually flows out of the osteotomy guide plate, which not only will not block the nail hole but can also play a role in assisting the substrate to cool down.

Of course, in consideration of the problem of storage and searching of a plurality of osteotomy guide plates during use, a convex mark 8 may be provided on the surface of the substrate 1, and the convex mark 8 may be a name or a short name of a patient, or the like.

A method for preparing a mandibula osteotomy guide plate is provided, comprising the steps of:

A. Parameter Design (1) creating data for the standardized part: using digital technology to create data for the osteotomy guide standardized part 2, the standardized sleeve 41, and the protective inner sleeve standardized part 6 respectively for later use;

wherein, in the creation of the data, the basic structure of the osteotomy guide standardized part 2 is a hollowed-out chamfered cuboid, and the size parameters (length×width×height) of the outer wall and the lumen are fixed values, and two fixed values are provided for the osteotomy guide standardized part 2 described in the present invention, one for the jawbone osteotomy guide plate and the other for the bone grafting osteotomy guide plate; the width of the lumen of the osteotomy guide standardized part 2 is matched with the thickness of the saw blade of an oscillating saw or sagittal saw used in the surgery, and the long diameter of the inner cavity is a fixed value, which is greater than the width of the standardized substrate, in order to provide additional space for the drainage of the osteotomy guide plate. The osteotomy guide through groove 21 in the osteotomy guide standardized part 2 in the surgery guides the surgeon to insert the oscillating saw or the sagittal saw into the groove for the osteotomy operation, and each of the independent osteotomy guide plates is equipped with one or more osteotomy guide standardized parts 2 of the same quantity as the that of osteotomy lines.

The basic structure of the standardized sleeve 41 is a cylindrical structure with fixed values in wall thickness, height and diameter. The inner wall of the standardized sleeve 41 is provided with two independent grooves for locking with the protective inner sleeve standardized part 6, and the size parameters of the groove are matched with the protective inner sleeve standardized part 6.

The basic structure of the protective inner sleeve standardized part 6 is a cylindrical structure, with fixed values in the wall thickness, height and diameter, and made of stronger materials than the standardized sleeve 41, such as stainless steel, titanium alloy, etc. The protective inner sleeve standardized part 6 is a 3D printed or machined part. A convex prismoid 61 is disposed on the outer wall of the protective inner sleeve standardized part 6, where the prismoid 61 is locked with a groove on the inner wall of the standardized sleeve 41. The size parameters of the prismoid 61 are matched with the outer wall of the protective inner sleeve standardized part 6.

(2) extracting data of the nail hole: importing a postoperative mandibular model and a postoperative bone graft model of a patient and conducting simulation matching, and obtaining a restoration model by 3D printing technology, shaping a metal graft 8 with a mounting hole 91 onto the restoration model, and perforating in the restoration model along the mounting hole by a drilling device to form a nail hole site; placing the restoration model with the nail hole site in a 3D scanner for scanning, and then establishing the fitting parameter cylinder in the space of the nail hole site, wherein the parameter distribution range of the fitting parameter cylinder covers the postoperative bone stump and the bone surface after the bone grafting, the data of the nail hole is extracted according to the fitting parameter cylinder, and the new model with the nail hole feature is saved for the subsequent design processes;

(3) creating data for the hole-free guide plate: importing a pre-operative mandibular model, confirming the coverage area of the substrate 1 and the position of the osteotomy line according to the surgical plan, and generating a model of the substrate 1, wherein the undulating condition of the inner side of the substrate 1 is matched with that of the surface of the preoperative mandibular model, and the substrate 1 covers the whole osteotomy line; and then, importing the data of the osteotomy guide standardized part 2, selecting the data of the osteotomy guide standardized part 2 adapted to the substrate 1, and extracting a main inertia axis of the osteotomy guide standardized part 2 (i.e., the axis for guiding the direction of the osteotomy line) using digital technology, matching the axis with the axial position of the mandibular osteotomy line, that is, obtaining the osteotomy guide through groove 21 accurately placed at the axis of the osteotomy line; and (4) creating the data of the osteotomy guide plate: importing the data of the nail hole and the data of the standardized sleeve 41, extracting the main inertia axis of the standardized sleeve 41 by digital technology, matching the main inertia axis with the data of the nail hole 4, and setting the distance between the top end of each standardized sleeve 41 and the bone surface to a fixed value, in order to match the data of the standardized sleeve 41 respectively with the data of the nail hole 4, then using digital technology to create a cylinder of the expected size, moving the cylinder to the expected position and axially passing through the model of the substrate 1, and cutting the model of the substrate 1 by Boolean operation function, completing the creation of the guide plate retention hole 3, and finally finishing the design of all parameters of the osteotomy guide plate;

B. Model Printing importing the parameters of the osteotomy guide into a 3D printer for printing, and then embedding the printed protective inner sleeve standardized part 6 in the standardized sleeve 41 to obtain the osteotomy guide plate.

Figure 7:
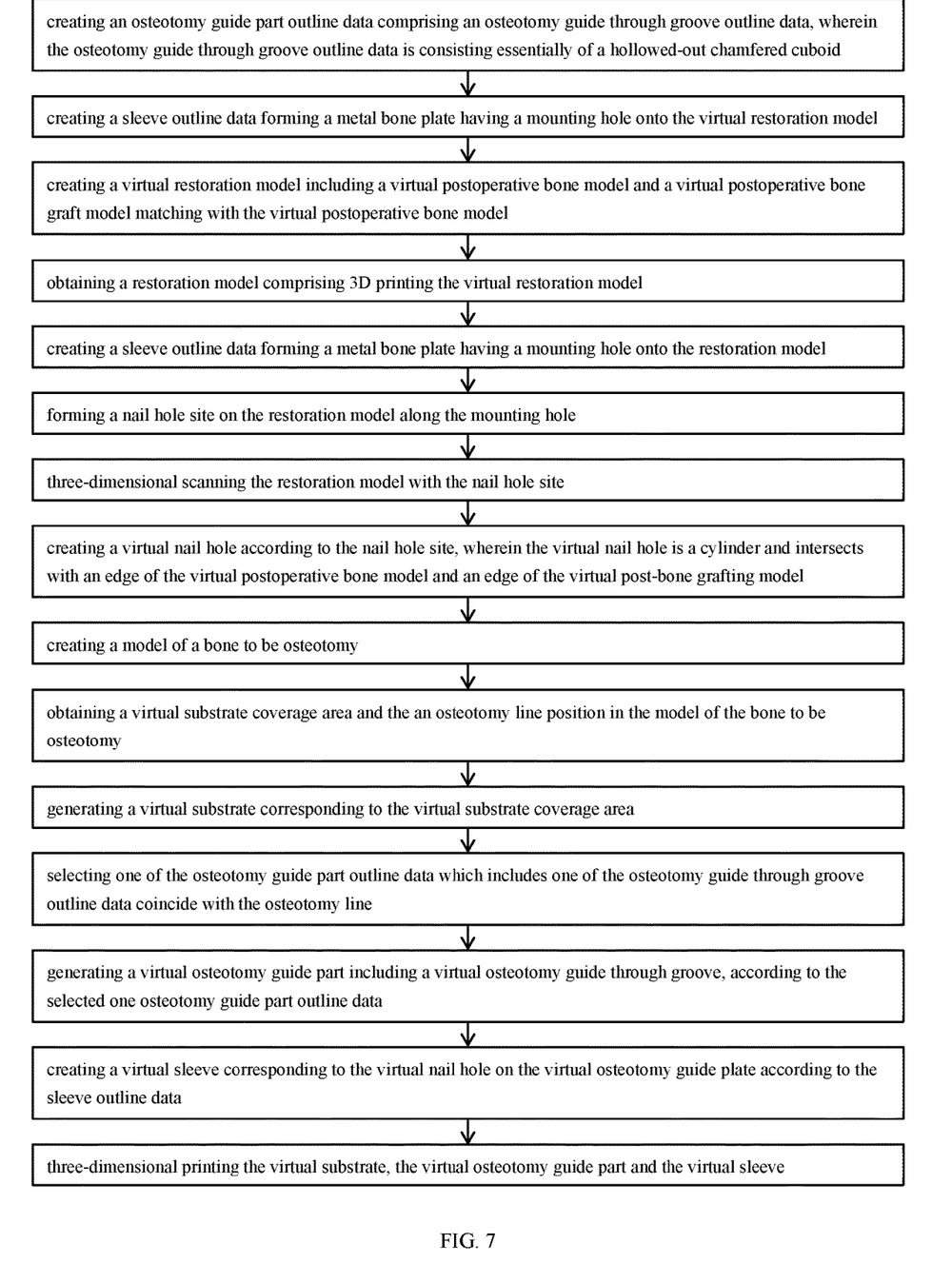
FIG. 7 is a flow chart of a method for preparing an osteotomy guide plate according to an embodiment of the present application.

According to an embodiment of the present application, a method for preparing an osteotomy guide plate, is shown in FIG. 7.

Embodiment 2

Figure 5:
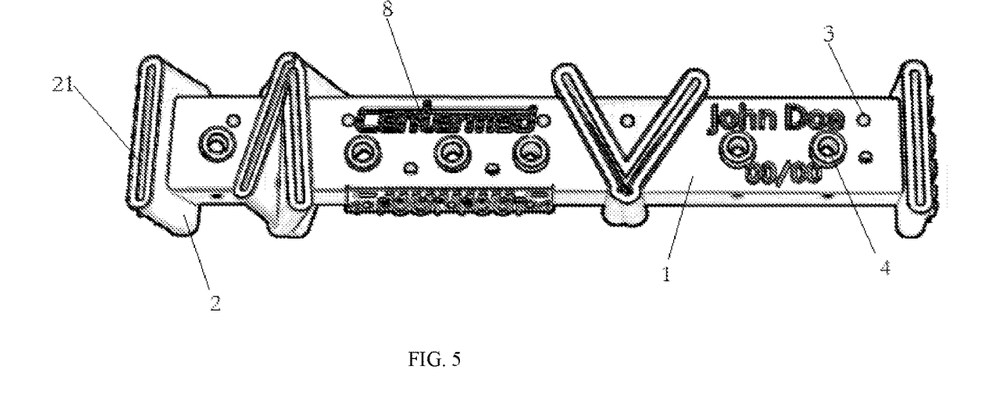
FIG. 5 is a schematic structural view of a mandibular osteotomy guide plate according to embodiment 2 of the present invention.

As shown in FIG. 5, the present invention provides a fibula osteotomy guide plate. Unlike the embodiment 1, the substrate of the fibula osteotomy guide plate is a cuboid standardized part. When preparing the fibula osteotomy guide plate, the creating the data of the substrate 1 comprises generating a parameter fitting cuboid in the coverage area of the fibula model firstly, and then selecting the data of the appropriate cuboid standardized part to be imported, and matching the main inertia axis of the cuboid standardized part with the parameter cuboid to obtain the substrate 1 adapted to the appropriate position. The other steps are the same as in the embodiment.

The jawbone osteotomy guide plate of the present invention is used as follows:

1. the surgeon entrusts the relevant personnel to perform ethylene oxide sterilization to the mandibular osteotomy guide plate, and then delivers the sterilized mandibular osteotomy guide plate to the operating room;

2. the surgeon then exposes the jawbone operation area after opening the flap, and then places the mandibular osteotomy guide plate at the osteotomy position and fixes it with a metal screw at the nail hole 4. It then inserts the osteotomy guide through groove 21 using a sagittal saw or an oscillating saw (conventional operating room power system) for osteotomy operation;

3. the surgeon or the assistant uses the syringe filled with physiological saline to inject the physiological saline into the substrate 1 through the drainage channel 7 to flush the bone fragments out of the inner wall of the substrate 1 and assist the substrate 1 to cool down; and 4. the surgeon inserts the drilling device (the drill bit connected to the power system or the handle) into the protective inner sleeve standardized part 6 for drilling operation. The surgeon or the assistant uses the syringe filled with the physiological saline to inject the physiological saline into the substrate 1 through the drainage channel in the same way, in order to flush the bone fragments out of the inner wall of the substrate 1 and assist the substrate 1 to cool down. After use of the mandibular osteotomy guide plate, the retention screw, and the mandibular osteotomy guide plate are removed.

The fibula osteotomy guide plate of the present invention is used in a different way from that of the mandibular osteotomy guide plate in that: the osteotomy operation and the drilling positioning are performed on the fibula using the fibular osteotomy guide plate. Then, the titanium plate nails are placed on the cut bone graft segment (possibly together with the blood vessel) according to the nail hole site in the fibula osteotomy guide plate, and the fibula bone graft segment with the fixed titanium plate nails is transplanted into the jawbone segment, and the other screws are fixed through the guide plate retention hole 3.

The above only describes specific embodiments of the present invention, but the scope of the present invention is not limited thereto, and any change or substitution that can be easily conceived by those skilled in the art within the disclosed technical scope of the present invention should be covered by the scope of the present invention. Therefore, the scope of the invention should be determined by the scope of the appended claims.

What is claimed is:

1. A computer-implemented method for preparing an osteotomy guide plate, comprising:

creating an osteotomy guide part outline data comprising an osteotomy guide through groove outline data, wherein the osteotomy guide through groove outline data is consisting essentially of a hollowed-out chamfered cuboid;

creating a sleeve outline data;

creating a virtual restoration model comprising a virtual postoperative bone model and a postoperative bone graft model;

obtaining a restoration model comprising 3D printing the virtual restoration model;

forming a metal bone plate having a mounting hole onto the restoration model;

forming a nail hole site on the restoration model along the mounting hole;

three-dimensional scanning the restoration model with the nail hole site;

creating a virtual nail hole according to the nail hole site, wherein the virtual nail hole comprises a cylinder and intersects with an edge of the virtual postoperative bone model and an edge of the postoperative bone graft model;

creating a model of a bone to be cut;

obtaining a virtual substrate coverage area and an osteotomy line position in the model of the bone to be cut;

generating a virtual substrate corresponding to the virtual substrate coverage area;

selecting one of the osteotomy guide part outline data which comprises one of the osteotomy guide through groove outline data coinciding with the osteotomy line;

generating a virtual osteotomy guide part comprising a virtual osteotomy guide through groove, according to the selected one osteotomy guide part outline data;

creating a virtual sleeve corresponding to the virtual nail hole on the virtual osteotomy guide plate according to the sleeve outline data; and three-dimensional printing the virtual substrate, the virtual osteotomy guide part and the virtual sleeve, for obtaining the osteotomy guide plate comprising a substrate, osteotomy guide part and a sleeve.

2. The method according to claim 1, wherein the bone to be cut is a mandible.

3. The method according to claim 1, wherein the bone to be cut is a fibula.

4. The method according to claim 1, wherein a surface of the substrate comprises a convex mark.

\* \* \* \* \*